(12) United States Patent
Treschow et al.

(10) Patent No.: US 7,645,603 B2
(45) Date of Patent: Jan. 12, 2010

(54) CELLS HAVING CARDIAC GLYCOSIDE RESISTANCE

(75) Inventors: Alexandra Treschow, Stockholm (SE); Sirac Dilber, Huddinge (SE); Alar Aints, Stockholm (SE)

(73) Assignee: Avaris AB, Huddinge (SE)

( * ) Notice: Subject to any disclaimer, the term of this patent is extended or adjusted under 35 U.S.C. 154(b) by 515 days.

(21) Appl. No.: 10/545,491

(22) PCT Filed: Feb. 13, 2004

(86) PCT No.: PCT/SE2004/000197

§ 371 (c)(1),
(2), (4) Date: Mar. 27, 2006

(87) PCT Pub. No.: WO2004/072278

PCT Pub. Date: Aug. 26, 2004

(65) Prior Publication Data

US 2006/0228343 A1 Oct. 12, 2006

Related U.S. Application Data

(60) Provisional application No. 60/449,556, filed on Feb. 25, 2003.

(30) Foreign Application Priority Data

Feb. 14, 2003 (SE) .................................. 0300412

(51) Int. Cl.
*C12N 9/10* (2006.01)
*C12N 9/00* (2006.01)
*C12N 1/20* (2006.01)
*C12N 15/00* (2006.01)
*C07H 21/04* (2006.01)

(52) U.S. Cl. .................... 435/193; 435/183; 435/252.3; 435/320.1; 536/23.2

(58) Field of Classification Search .................. None
See application file for complete search history.

(56) References Cited

U.S. PATENT DOCUMENTS 6,309,874 B1 10/2001 Belusa

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report mailed May 11, 2004, for international application No. PCT/SE2004/000197, filed Feb. 13, 2004, 5 pages.
Aints, Alar et al. (May 20, 2002) "Enhanced Ouabain Resistance Gene as a Eukaryotic Selection Marker," Human Gene Therapy, 13: 969-977.
Askew, G. Roger et al. (Sep. 30, 1994) "Identification of an Amino Acid Substitution in Human α1 Na, K-ATPase which Confers Differentially Reduced Affinity for Two Related Cardiac Glycosides," Journal of Biological Chemistry, 269(39): 24120-24126.
Choy, W. N. et al. (1980) "SG 2201: Two Periods of Enhanced Mutagenesis to Ouabain Resistance During DNA Synthesis in Synchronized Diploid Human Lymphoblasts," Journal of Cell Biology, 87(2, Part 2): 286A.
Elmore, Eugene et al. (1982) "Measurement of Spontaneous Mutation Rates at the $Na^+/K^+$ATPase Locus (Ouabain Resistance) of Human Fibroblasts Using Improved Growth Conditions," Mutation Research, 97: 393-404.
Emanuel, Janet R. et al. (Sep. 1989) "Identification of a Region within the Na, K-ATPase α Subunit That Contributes to Differential Ouabain Sensitivity," Molecular and Cellular Biology, 9(9): 3744-3749.
Kumar, Anil et al. (1987) "Absence of Gene Amplification in Human Cell Mutants Resistant to Cardiac Glycosides," Molecular and Cellular Biochemistry, 78: 73-79.
Price, Elmer et al. (1988) "Structure-Function Relationships in the Na, K-ATPase α Subunit: Site-Directed Mutagenesis of Glutamine-111 to Arginine and Asparagine-122 top Aspartic Acid Generates a Ouabain-Resistant Enzyme," Biochemistry, 27:8400-8408.
Yamamoto, S. et al. (1996) "Modulation of Pump Function by Mutations in the First Transmembrane Region of $Na^+$-$K^+$-ATPase $α_1$-subunit," Am. J. Physiol., 270 (Cell Physiol. 39): C457-C464.

* cited by examiner

*Primary Examiner*—Christian L Fronda
(74) *Attorney, Agent, or Firm*—Morrison & Foerster LLP

(57) ABSTRACT

An isolated cell having a nucleic acid construct encoding a recombinant Na+, K+-ATPase α1-subunit protein resistant to cardiac glycosides, e.g., ouabain, is disclosed. Selected amino acid substitutions in the normal human Na+, K+-ATPase α1-subunit confers resistance to cardiac glycosides. Cardiac glycoside resistant Na+, K+-ATPase α1-subunits may be useful as selection markers in gene therapy and research applications.

35 Claims, 2 Drawing Sheets

CELLS HAVING CARDIAC GLYCOSIDE RESISTANCE

CROSS REFERENCE TO RELATED APPLICATIONS

This application is a U.S. national phase application of International application number PCT/SE2004/000197, filed Feb. 13, 2004, which claims priority to Swedish Application Serial No. SE 0300412-4 filed Feb. 14, 2003 and U.S. Provisional Application Ser. No. 60/449,556 filed Feb. 23, 2003, all of which are hereby incorporated by reference in their entirety.

FIELD OF THE INVENTION

The present invention relates to the field of biotechnology, and in particular to a recombinant human protein and the corresponding nucleic acid construct, as well as to methods of their use in therapy and research, said protein being resistant to cardiac glycosides, in particular an ouabain resistant $Na^+$, $K^+$-ATPase alpha1 subunit.

BACKGROUND OF THE INVENTION

Gene therapy is an approach to treat diseases either by modifying the expression of one or more genes of an individual, or by correcting abnormal genes. By administration of DNA rather than a drug, many different diseases are currently being investigated as candidates for gene therapy. These include genetic disorders, e.g. cystic fibrosis, cardiovascular disease, various forms of cancer, as well as infectious diseases such as AIDS. When transferring genes to cells ex vivo or in vivo, a selection is often required, if the gene modified cells do not have a selective advantage over unmodified cells. It could also be desirable to ensure sufficient multiplication of the cells having received the new gene before transferring them to the patient.

The practical use of gene therapy is still limited due to various reasons, one of them being low gene transfer efficiency and the requirement for extended in vitro cell culture selection to obtain enriched or pure populations of gene modified cells. Different marker genes for selection of gene-modified cells have hitherto been used. These fall into two categories: cell surface markers and metabolic selection markers.

Cells modified by cell surface marker genes can be selected by fluorescence-activated cell sorting (FACS) or by immunomagnetic techniques. Cell surface markers usually allow fast selection procedures, but there is a risk of false-positive selection if the selection is performed too early following the transduction, due to transfer of the marker protein in the retroviral envelope to the target cell plasma membrane. Further, FACS is an open system leading to difficulties in maintaining sterility. In addition, sorting large amounts of cells takes considerable time. A general drawback of immunomagnetic sorting is the low recovery of gene-modified cells. Only cells with high transgene expression are efficiently sorted. Low recovery requires larger volumes of starting materials and is economically unfavourable.

Metabolic selection markers allow for efficient background-free selection of the gene-modified cells, but the duration of selection is usually long, typically lasting about one week to ten days. The selection substance may also be directly DNA damaging.

Further, there is a great risk of non-human genes or gene fragments to trigger an immune response against gene modified cells. Thus, human cells modified with these genes would be eliminated by the immune system. Immunogenicity is usually not a problem with cell surface markers since these are generally human. In contrast, metabolic selection markers are often of non-mammalian origin, documented to cause immunogenicity problems.

Another problem with current selection markers is their putative influence on normal cell functions. This poses a risk of causing cell alterations which might contribute to cell transformation.

$Na^+$, $K^+$-ATPase is a housekeeping enzyme present in all mammalian cells. It is an integral membrane protein that establishes the electrochemical gradient across the plasma membrane by transporting sodium ions out of the cell and potassium ions into the cell (in the ratio 3:2), utilising ATP hydrolysis as an energy source. Variations in the activity of the $Na^+$, $K^+$-ATPase have effects on a number of critical cell functions. The minimal functional enzyme active in the membrane is a dimer consisting of an α-subunit and a β-subunit. Four isoforms ($\alpha_1$, $\alpha_2$, $\alpha_3$, and $\alpha_4$) of the $Na^+$, $K^+$-ATPase α-subunit gene family have been cloned in man and rat, the $\alpha_1$ being the most resistant isoform to cardiac glycosides.

Cardiac glycosides are naturally occurring compounds found to have an effect on the contractive power and rhythm of the mammal heart. Examples include digoxin and digitoxin, from woolly foxglove (*Digitalis lanata*) and from common foxglove (*Digitalis purpurea*); proscillaridine A from sea squill, (*Urginea* (*Scilla*) *maritime*), ouabain (G-strophantine) from *Strophantus gratus*; convallatoxin from mayflower (Lily-of-the-valley, *Convallaria majalis*); and palytoxin from the coral *Palythoa toxica*. All cardiac glycosides seem to comprise a steroidal part, coupled to one or more glucose like molecules.

Ouabain, one member of the above group of drugs, has been shown to bind to the α-subunit and inhibits the ATPase and ion-transport activity of the enzyme. In this description, ouabain is used as one example of cardiac glycosides.

As mentioned above, current selection methods have several shortcomings negatively influencing the cell selection. Accordingly, there is a need for a rapid selection marker for use in in vitro applications as well as in human gene therapy with high efficiency and minimal immunogenicity. Such a marker would also have wide application in methods for studying the toxicology of drugs, studying the mechanisms of toxicity, screening for new drugs in vitro, etc.

One objective of the present invention is to make available such a marker, as well as methods of its production and use. Further objectives, the solutions offered by the invention, as well as their advantages will be evident to a skilled person upon study of the following description and examples.

PRIOR ART

There is a large naturally occurring difference in ouabain sensitivity among different mammalian species. Rat and mouse $Na^+$, $K^+$-ATPase proteins exhibit high resistance to cardiac glycosides, whereas human sheep, monkey and pig proteins are highly sensitive (Kuntzweiler et al., *J. Biol. Chem.*, 271: 29682-29687, 1996). As early as 1988, Price and Lingrell (*Biochemistry*, 1, 27: 8400-8408), suggested that the determinants involved in ouabain sensitivity of the sheep protein are located in the amino-terminal half of the $Na^+$, $K^+$-ATP α subunit. Several attempts have been made to increase the resistance of different, non-human $Na^+$, $K^+$-ATPases, however with varying success and a highly resistant phenotype of rat $Na^+$, $K^+$-ATPase has not been reached.

U.S. Pat. No. 6,309,874 (Belusa) presents a selection system based on the rat $Na^+$, $K^+$-ATPase $\alpha_1$ gene comprising point mutations at the amino acid positions 799 and/or 801 and transfected into non-human mammalian cell lines.

Coppi et al. (Biochemistry, 38:24942505, 1999) studied the effects of combinations of charged residues at the M1-M2 loop border on ouabain affinity of the $\alpha_1$ and $\alpha_2$ rat isoforms. They report that the ouabain sensitivity of the rat $Na^+$, $K^+$-ATPase is dependent not only on the identity of the M1-M2 loop border residues but also on the environment into which they are introduced. They also suggest that these residues might affect ouabain sensitivity by destabilizing or altering the E2 conformation of the $Na^+$, $K^+$-ATPase to which ouabain preferentially binds.

De Fusco et al. (Nature Genetics, 33:192-196, 2003— published 21 Jan. 2003) studied mutations in the gene encoding the $\alpha_2$ subunit of human $Na^+$, $K^+$-ATPase and their association with familial hemiplegic migraine type 2. To investigate the ion transport function of mutated $\alpha_2$ and $\beta_2$ subunits they used the $Na^+$, $K^+$-ATPase activity. The $\alpha_2$ and $\beta_2$ subunits were made ouabain resistant by introducing two amino acid mutations, Q116R and N127D, in the first extra cellular loop. However, the homology at the amino acid level between the $\alpha_1$ and $\alpha_2$-isoforms in human $Na^+$, $K^+$-ATPase is low, i.e. only about 87%, and performing the same mutations in the $\alpha_1$-gene can therefore not be assumed to have the same desired effect.

Aints et al. (*Human Gene Therapy*, 13:969-977, 2002) achieved increased resistance to ouabain in human cells using the rat $Na^+$, $K^+$-ATPase $\alpha_1$ subunit, in which leucine at position 799 was substituted for a cysteine by targeted mutagenesis.

Emanuel et al. (Mol. Cell Biol., 9:3744-3749, 1989) studied determinants within the $Na^+$, $K^+$-ATPase $\alpha$ subunit that contribute to differential ouabain sensitivity. They constructed chimeric cDNA molecules between ouabain-resistant and ouabain-sensitive $\alpha$ subunit cDNAs. By substituting the 5' end of the human $\alpha 1$ subunit with the 5' end of rat $\alpha 1$ cDNA Emanuel et al. obtained a recombinant protein comprising, in the amino terminal, 172 amino acid residues of the rat $\alpha 1$ subunit. The construct was transfected into African green monkey CV-1 cells and the recombinant $Na^+$, $K^+$-ATPase showed to be resistant to $10^{-4}M$ ouabain. However, this construct was never transfected into human cells and the functionality and immunogenicity of said construct in human cells can be not be estimated from this study. A construct with such a large substitution deriving from a rat gene is likely to confer high immunogenicity in human cells and is therefore not suitable as a selection marker for use in human gene therapy.

In conclusion, the prior art describes the $Na^+$, $K^+$-ATPase biology but does not provide evidence to the identification of amino acids conferring increased resistance to ouabain in the human $Na^+$, $K^+$-ATPase $\alpha 1$ subunit and therefore does not succeed in providing evidence to, or suggestion for the human $Na^+$, $K^+$-ATPase $\alpha 1$ gene to develop into an efficient selection marker for human gene therapy. In conclusion, there remains a need for a non-immunogenic, rapid and reliable selection marker for use in human gene therapy and research.

SUMMARY OF THE INVENTION

The present invention relates to a recombinant human $Na^+$, $K^+$ ATPase protein with increased cardiac glycoside resistance, and in particular to a recombinant human $Na^+$, $K^+$ ATPase $\alpha 1$-subunit polypeptide conferring such increased cardiac glycoside resistance. The said recombinant protein is at least 98% homologous to the corresponding human $Na^+$, $K^+$ ATPase $\alpha 1$-subunit at amino acid level. The dissimilarity in amino acid sequence between the recombinant $\alpha 1$-subunit and the corresponding human $Na^+$, $K^+$ ATPase $\alpha 1$-subunit is situated between and including the amino acids corresponding to number 65-133 of the human $Na^+$, $K^+$ ATPase $\alpha 1$-subunit of SEQ ID NO. 1 or equivalent functional homologues thereof.

The attached sequence listing (prepared using the Patentin 3.1 software) discloses the amino acid sequence for a human wild type $Na^+$, $K^+$-ATPase $\alpha 1$-subunit (SEQ ID NO. 1), the amino acid sequence of a recombinant $Na^+$, $K^+$-ATPase according to one embodiment of the invention (SEQ ID NO. 2), and the recombinant nucleic acid coding sequence corresponding to said protein (SEQ ID NO. 3). The primers used in the examples are disclosed as SEQ ID NO. 4-21. The amino acid sequence exhibiting the minimal 2 amino acid substitutions is disclosed as SEQ ID NO. 23 and the corresponding coding sequence as SEQ ID NO. 24, both constituting a preferred embodiment of the invention.

Further aspects of the invention and their advantages will become evident from the following description, example, drawings and the attached claims, incorporated herein by reference.

BRIEF DESCRIPTION OF THE DRAWINGS

The invention will be described in closer detail in the following description, examples, and attached drawings, in which.

DETAILED DESCRIPTION OF THE INVENTION

Figure 1:
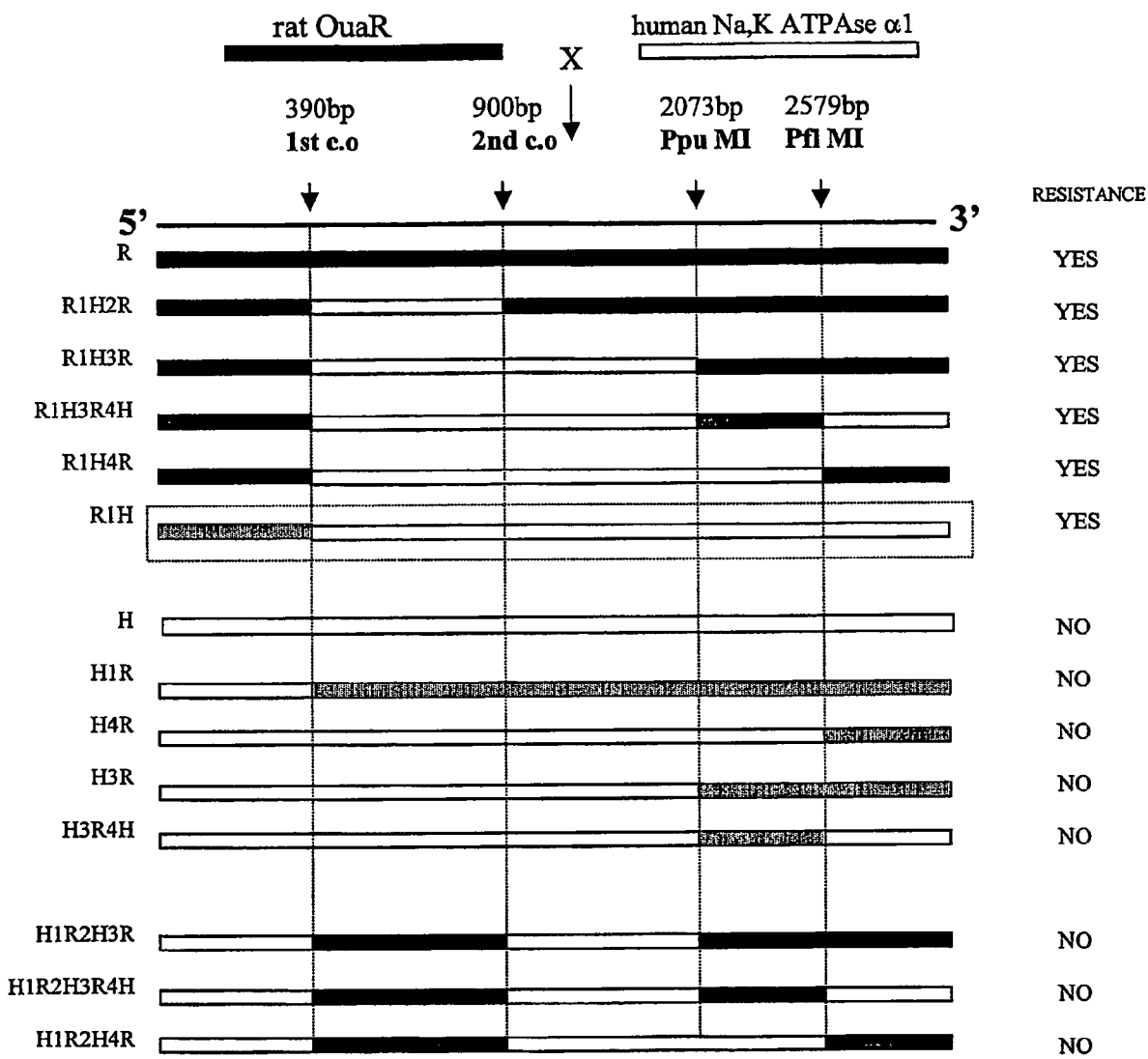
FIG. 1 shows a schematic representation of the constructs that were tested for resistance to ouabain induced cell death. HeLa and COS-7 cells transfected with plasmids containing these constructs were incubated in 10 μM ouabain for 24 hours and 4 days respectively, followed by analysis. The top six constructs conferred resistance to ouabain induced cell death, while the eight constructs below did not.

In the context of the present description and claims, the term "functionally homologous" or "functional equivalent" refers to a property of sequences sharing perhaps a lower structural homology with the disclosed sequence, but exhibiting homologous function in vivo and/or in vitro, in either the healthy or the diseased organism, e.g. coding the same or highly similar proteins sharing the same or highly similar cellular functions. The most relevant cellular functions are in this case the increase resistance to cardiac glycosides, and the low or non-existing immunogenicity.

The present invention relates to a new and efficient selection marker for use in cell culture experiments and in molecular biology, e.g. for the selection of human cells. The invention is based on a gene that is naturally expressed in all cells, i.e. the $Na^+$, $K^+$-ATPase $\alpha 1$ subunit gene. By minimal alteration of normal protein activity an efficient selectable marker for use in human gene therapy is established that allows for rapid elimination of unmodified human cells with ouabain and efficient recovery of gene modified cells. Due to minimal alteration of a naturally occurring gene, the selection marker confers no or very low immunogenicity.

The present invention is based inter alia on the results from an experiment wherein the nucleotide sequence coding for the first about 130, preferably the first 133 amino acids in the amino terminal of the human Na$^+$, K$^+$-ATPase α1 subunit cDNA was substituted with the corresponding part of the rat Na$^+$, K$^+$-ATPase α1 subunit cDNA. The rat homologue of the human Na$^+$, K$^+$-ATPase α1 subunit confers significantly higher resistance to ouabain toxicity. The present inventors have surprisingly shown that the chimeric α1-subunit coded by this chimeric cDNA exhibits a significantly increased resistance to the cardiac glycoside ouabain compared to human Na$^+$, K$^+$-ATPase α1. The chimeric α1-subunit codes for a different amino acid at ten positions from the human α1-subunit. Thus, the difference between the chimeric α1-subunit and the wild type human α1-subunit at protein level are ten amino acid substitutions.

When considering the aspect of the invention relating to the selection of gene-modified cells, it is underlined that the selection process relies on a particularly rapid elimination of human cells by ouabain via inhibition of ion transport across the plasma membrane. Therefore, the selection process is not genotoxic and this is, to the best knowledge of the inventors, the first time when high ouabain resistance has been obtained for a substantially human gene. The resulting unprecedented level of resistance makes it possible to utilize this mutated gene as a selection marker for very rapid elimination of unmodified human cells. This marker may have applications in gene therapy applications for a wide array of human diseases and disabilities, as well as for genetic modifications of cells in culture.

Moreover, this selection marker can advantageously be used together with so called suicide genes, genes inducing cell death.

The present invention is based on a gene expressed in all cell types and provides an advantageous selection system to current selection/sorting markers. Since the amino acid sequence encoded for by the nucleic acid construct of the invention has at least 98%, and preferably more than 99% homology to the human wild type Na$^+$, K$^+$-ATPase α1-subunit, the probability of immunogenicity is highly unlikely.

An additional advantage is that ouabain is a well-known, relatively inexpensive pharmaceutical; it has been widely used in the clinic as a cardiac medicine. Ouabain has no known toxic effects apart from its action as an inhibitor of Na$^+$, K$^+$-ATPase, it can be quickly removed form a cell culture by a simple wash and gives no false-positive selection. Its rapid course of action in the cell culture settings allows for quick selection of transiently transfected or stably transduced cells. In summary, the selection is rapid, 24-48 h in most cell types, and does not give false positive results. These properties can make this human mutated construct a favoured selection marker for use in pre-clinical and clinical molecular medicine.

Ouabain binds to Na$^+$, K$^+$-ATPase extracellularly and the junction between the first and second transmembrane spanning regions (H1-H2 junction) is believed to strongly influence the level of ouabain resistance of the α1-subunit. The H1-H2 junction exposed extracellularly include amino acids number 118-129 (the numbering established according to SEQ ID NO. 1 or functionally equivalent homologues thereof), Four of five consistent interspecies residue differences in the first about 130 amino acids are in the H1-H2 junction, i.e. corresponding to the amino acids no. Q118, A119, Q126, and N129 in the human Na$^+$, K$^+$-ATPase α1-subunit sequence of SEQ ID. NO. 1 or the corresponding amino acids in functionally equivalent homologues thereof. The membrane anchored residues flanking the H1-H2 junction are also believed to be important for ouabain affinity.

One aspect of the invention is a recombinant Na$^+$, K$^+$ ATPase α1-subunit, said recombinant protein is at least 98% homologous to the corresponding human Na$^+$, K$^+$ ATPase α1-subunit at the amino acid level, wherein the amino acid sequence of said human protein is the sequence of SEQ ID. NO. 1 or any functionally equivalent homologue thereof, and where the recombinant Na$^+$, K$^+$ ATPase α1-subunit is more resistant to ouabain than the corresponding human protein.

The inventors have shown that the location of the substitutions is of significant importance. Consequently, a preferred aspect of the invention is a recombinant Na$^+$, K$^+$ ATPase α1-subunit, wherein the differences between said protein and the corresponding human Na$^+$, K$^+$ ATPase α1-subunit are situated within the first about 130 amino acids, wherein the amino acid sequence of said human protein is the sequence of SEQ ID NO. 1, or any functionally equivalent homologue thereof.

The work performed by the present inventors has demonstrated that said differences in the amino acid sequence between the α1-subunit of said protein and the corresponding human Na$^+$, K$^+$ ATPase α1-subunit are preferably situated between and including the amino acids number 65-133, and most preferably limited to at least one of the amino acids situated between and including the amino acids number 117-130 (comprising also the first membrane anchored residues flanking the H1-H2 junction) wherein the amino acid sequence of said human protein is the sequence of SEQ ID NO. 1, or any functionally equivalent homologue thereof. In one embodiment of the present invention the said protein differs from the corresponding human Na$^+$, K$^+$ ATPase α1-subunit with respect to a maximum of 10 of the amino acids situated between and including the amino acids number 117-130, more preferably a maximum of 4 of the amino acids situated between and including the amino acids number 117-130, and most preferably a maximum of 2 of the amino acids situated between and including the amino acids number 117-130, wherein the amino acid sequence of said human protein is the sequence of SEQ ID. NO. 1 or any functionally equivalent homologue thereof.

In one embodiment the recombinant α1-subunit differs from the corresponding human Na$^+$, K$^+$ ATPase α1-subunit in the identity of the amino acids number 118 and 129, most preferably the mutations Q118R and N129D, wherein the amino acid sequence of said human protein is the sequence of SEQ ID NO. 1 or any functionally equivalent homologue thereof.

A recombinant protein according to the present invention exhibits high resistance to ouabain; and preferably said protein is resistant to ouabain, at least at an ouabain concentration of $10^{-7}$ M. More preferably said protein is resistant to an ouabain concentration of at least $10^{-5}$ M and most preferably at least $10^{-3}$ M.

The present invention makes available a recombinant Na$^+$, K$^+$ATPase α1-subunit, as defined above, further characterized in that the said protein comprises the amino acid sequence of SEQ ID NO. 2 or any functionally equivalent homologue thereof, preferably the sequence of SEQ ID NO. 23 or any functionally equivalent homologue thereof.

Another aspect of the invention is a nucleic acid construct encoding the recombinant Na$^+$, K$^+$ ATPase protein α1-subunit having at least 98% homology to human Na$^+$, K$^+$-ATPase α1-subunit as defined above, and in particular a nucleic acid construct wherein the encoded amino acid sequence differ from the corresponding human Na$^+$, K$^+$ ATPase α1-subunit in amino acid residues situated between and including the amino acids corresponding to number 65-133 of SEQ ID NO. 1 or any functionally equivalent homologue thereof. When the construct is expressed in a cell it confers increased resistance to cardiac glycosides and other Na$^+$, K$^+$ ATPase inhibitors and especially one of, but not limited to, ouabain, digoxin and digitoxin, proscillaridine A, palytoxin and convallatoxin.

According to one embodiment of the invention, the nucleic acid construct comprises the sequence given in SEQ ID NO. 3, or a functionally equivalent homologue thereof.

The present invention also makes available a new method for producing a recombinant, ouabain resistant Na$^+$, K$^+$ ATPase α1-subunit as defined above. In this method, the 5'-end of the human Na$^+$, K$^+$ ATPase α1-subunit cDNA is modified to produce a recombinant protein that is at least 98% homologous to the corresponding human Na$^+$, K$^+$ ATPase α1-subunit at amino acid level, said modifications are amino acid substitution situated between and including the amino acids number 65-133 of SEQ ID NO. 1 or any functionally equivalent homologue thereof.

According to one embodiment of the inventive method the 5'-end of the human Na$^+$, K$^+$ ATPase α1-subunit cDNA is modified to introduce at least one site-directed mutation in the coding sequence, thereby substituting at least one amino acid with respect to the amino acids between and including the amino acids number 117-130 wherein the amino acid sequence of said human protein is the sequence of SEQ ID. NO. 1 or any functionally equivalent homologue thereof.

According to another embodiment of the method according to the invention, the 5'-end of the human Na$^+$, K$^+$ ATPase α1-subunit cDNA is modified to introduce specific changes of the amino acids sequence of the protein, said changes consisting of a maximum of 10 site-directed mutations in the coding sequence, thereby substituting amino acids situated between and including the amino acids number 117-130, more preferably a maximum of 4 substitution of the amino acids situated between and including the amino acids number 117-130, and most preferably a maximum of 2 substitution of the amino acids situated between and including the amino acids number 117-130 wherein the amino acid sequence of said human protein is the sequence of SEQ ID NO. 1, or any functionally equivalent homologue thereof.

In one embodiment of the inventive method, the recombinant α1-subunit is modified to differ from the corresponding α1-subunit of the human Na$^+$, K$^+$ ATPase protein in the amino acids number 118 and 129 (sequence numbering according to SEQ ID NO. 1 or the corresponding amino acids in functional equivalent homologues thereof), and most preferably the substitutions Q118R and N129D. The corresponding sequences are attached as SEQ ID NO. 23 (protein) and SEQ ID NO. 24 (coding sequence).

According to another embodiment of the method of the invention, the recombinant Na$^+$, K$^+$ ATPase α1-subunit confers resistance to at least $10^{-7}$ M ouabain when expressed in a cell. Preferably the nucleic acid construct confers resistance to at least $10^{-5}$ and more preferably at least $10^{-3}$ M ouabain.

The invention also relates to a method wherein the recombinant Na$^+$, K$^+$ ATPase α1-subunit of the invention confers resistance to other cardiac glycosides and other Na$^+$, K$^+$-ATPase inhibitors, such as, but not limited to, digoxin and digitoxin, proscillaridine A, palytoxin and convallatoxin.

Further, the present invention makes available a step in a method of gene therapy wherein a recombinant cardiac glycoside resistant marker, such as the ouabain resistant Na$^+$, K$^+$ ATPase α1-subunit as defined above, is used in methods for in vitro selection of gene-modified cells.

Methods for in vitro selection of gene-modified cells are well known to a person skilled in the art. In general terms, such methods can comprise the following steps: First, stable cultured cell lines or primary human cells of donor or patient origin are propagated in cell culture media. Second, gene transfer, i.e. transfer of genetic information in the form of natural, or synthetic, or modified nucleic acids or their analogues is performed with the help of electric, chemical or biological means, such as electroporation, transfection, or viral gene transfer (transduction). This however results in gene transfer only to a fraction of the cells.

Consequently, as a third step, the resulting gene-modified cell population needs to be isolated from the unmodified cells by separation, e.g. chemical selection: the transferred genetic material in addition to carrying a therapeutically active gene or genes, also carries a selectable gene conferring resistance to toxic substances, or medical drugs at toxic concentrations. Subjecting the modified and unmodified cell mixture to a toxic substance or a mixture of substances carries out the selection. The substance/es induce/s cell death in unmodified cells, but not in the gene-modified cell population. Thus, a pure population of gene-modified cells is obtained after selection.

According to the present invention, a cardiac glycoside such as ouabain is used as the toxic substance, and a nucleic acid sequence coding for the recombinant Na$^+$, K$^+$ ATPase α1-subunit conferring ouabain resistance as disclosed herein is included in the genetic material to be transferred.

Further, the present invention makes available a step in a method used for the study of mechanisms of toxicity wherein a recombinant cardiac glycoside resistant marker, such as the ouabain resistant recombinant Na$^+$, K$^+$ ATPase α1-subunit as defined above, is used in methods for in vitro or in vivo studies.

Methods for in vitro toxicity studies are well known to a person skilled in the art. In general terms, such methods can comprise, e.g. studies involving the induction of cell death using substances acting on the cell membrane ion channels and thus influencing the electrochemical gradient across the plasma membrane and ion homeostasis. In such studies, the test cells are grown in cell culture and the response of the cells to different test substances is registered. According to the present invention, the test cells are modified to express the ouabain resistant recombinant Na$^+$, K$^+$ ATPase α1-subunit construct and the change in the cell viability and pattern of cellular chemical signalling response is registered.

Further, the present invention makes available an ouabain resistant recombinant Na$^+$, K$^+$ ATPase α1-subunit as defined above for use in pharmacological studies of substances directly or indirectly influencing the human Na$^+$, K$^+$ ATPase.

A person skilled in the art knows various methods for pharmacological studies, and modifications of such methods can be made relying on literature and on the information disclosed in the present description and examples. In general, such studies involve induction of changes in cellular metabolism in response to chemical stimuli, or gene transfer. An example of such methods comprises the following steps: First, the test cells are grown in cell culture and the response of the cells to test substances or genetic manipulations is registered. According to the present invention, the cells are modified to express the ouabain resistant recombinant Na$^+$, K$^+$ ATPase α1-subunit construct and the change in the pattern of cellular functioning is registered. Pharmacological studies could also be performed in vivo.

The present invention also encompasses a nucleic acid construct as defined above or any functionally equivalent homologue thereof, wherein said construct forms a functional part of a gene-transfer vector. The transfer vector is preferably a plasmid, a viral vector, or any hybrid construct thereof.

Further, a particular embodiment of the present invention is a gene-modified natural, partly or completely synthetic cell comprising such nucleic acid construct as defined above or any functionally equivalent homologue thereof. Preferably said cell is a eukaryotic cell or a human chimeric cell, and most preferably a human cell.

Further, a particular embodiment of the present invention is a cell expressing the ouabain resistant recombinant $Na^+$, $K^+$ ATPase α1-subunit transferred by carriers such as exosomes and liposomes or functional equivalents thereof.

The present invention will be further described in the following non-limiting examples.

EXAMPLES

1. Materials and Methods 1.1 Constructs & Plasmids

A plasmid encoding the wild type rat $Na^+$, $K^+$-ATPase α1 (pCMVOuab$^r$) was purchased from Pharmingen (San Diego, Calif.). Human $Na^+$, $K^+$-ATPase α1 cDNA as a plasmid (phNKAa1) was kindly provided by J. B. Lingrel (Dept Mol Gene, Biochem and Microbiol, Univ Cincinnati College of Medicine, Cincinnati, Ohio). L-799 in pCMVOuabr was mutated to a cysteine by site-directed mutagenesis and named OuaR (Aints et al., *Human Gene Therapy*, 13:969-977, 2002). pEGFP-OuaR (pEGFPR) was made by inserting an ApaI-XbaI fragment from pCMV-OuaR between the ApaI and XbaI sites of pEGFP-C3 (Clontech, Palo Alto, Calif.). A pEGFP-hNKAα1 plasmid (pEGFPH) was made by inserting a NcoI (filled)-XbaI fragment from phNKAα1 between SmaI and XbaI in pEGFP-C1 (Clontech, Palo Alto, Calif.). The results in both cases were in-frame fusions between the inserted protein and EGFP. A pEGFP-hNKAα1-PX (H3R) chimeric fusion gene was made by substitution of the nucleotide sequence PfuMI-XbaI with the homologue fragment of pEGFP-OuaR. The pEGFP-hNKAa1-PV (H3R4H) and pEGFP-hNKAa1-VX (H4R) chimeric fusion genes were made by substitution of the nucleotide sequence PfuMI-Ppu MI and Ppu MI-XbaI with the homologue fragments of pEGFP-OuaR respectively. To make chimeras in the 5'-end of the $Na^+$, $K^+$-ATPase α1, segments of OuaR were amplified with the following primers:

```
                                          (SEQ ID NO. 4)
GGAACCTCAAAACGATAATCTGTACCTCGGGGTCGTGC,   (forward)

(SEQ ID NO. 5)
TCATCACGGGTGTGGCTGTGTTCCTGGGGGTGTCTT,     (forward)

(SEQ ID NO. 6)
AAGACACACCCAGGAACACAGCCACACCCGTGATGAGG,   (reverse)

(SEQ ID NO. 7)
AGCACCACACCCAGGTACAGATCATCATTTGGTGGTTCC,  (reverse)
and (SEQ ID NO. 8)
GGCAAGCTTGTTATCTAGA.                      (reverse)
```

Segments of pEGFPH were amplified with the following primers:

```
                                          (SEQ ID NO. 9)
GGAACCACCAAATGATGATCTGTACCTGGGTGTGGTGCT,  (forward)

(SEQ ID NO. 10)
CCTCATCACGGGTGTGGCTGTGTTCCTGGGTGTGTCTT,   (forward)

(SEQ ID NO. 11)
GCACGACCCCGAGGTACAGATTATCGTTTTGAGGTTCC,   (forward)

(SEQ ID NO. 12)
AAGACACCCCCAGGAACACAGCCACACCCGTGATGA,     (reverse)
and (SEQ ID NO. 13)
GCGAAGCTTGACGGGGGGCTAATAGTAGGT.           (reverse)
```

The primer:

```
CGGGATCACTCTCGGCATGGAC (forward) (SEQ ID NO. 14)
``` was used for both constructs. The crossover points were at position bp390 and bp900 from the 5'end of the gene. The chimeric constructs cloned by PCR were: H1R, R1H, R1H4R, R1H3R, R1H3R4H, H1R2H3R, H1R2H3R4H, H1R2H4R, R1H2R.

H=human, R=rat, 1=up to first cross over point, 2=up to second cross over point, 3=following PfuMI restriction site, 4=following Ppu MI restriction site. PCR products were gel purified and cloned into TOPO vectors (Invitrogen) and amplified by transformation of One-Shot *E. coli* (Invitrogen) according to the protocols supplied by the manufacturer. Plasmids were purified from the bacteria using the Quiaprep miniprep (Quiagen) according to the protocol supplied by the manufacturer. The PCR constructs were excised from the Hind III sites in the plasmids and gel purified. The fragments were inserted into the Hind III site in the EGFP-C1 or EGFP-C3 plasmids (Clontech, Palo Alto, Calif.) to create an in frame fusion with EGFP. All constructs with the 5'-end of rat gene sequence were inserted into the EGFP-C3 plasmid and constructs with the 5'-end of human sequence were inserted into the EGFP-C1 plasmid. The plasmids were amplified in One-Shot *E. coli* (Invitrogen) and purified using Quiaprep miniprep (Quiagen). Constructs were confirmed by restriction enzyme mapping and partial sequencing.

1.2 Transfection and Ouabain Toxicity Assay

HeLa cells (ATCC, Manassas, Va.) were cultured in DMEM Glutamax with 10% heat-inactivated fetal bovine serum (FBS). For transfections, Fugene 6 reagent (Roche Boehringer Mannheim, Germany) was used according to manufacturer's description. Briefly, 2 μg of plasmid DNA per $10^5$ cells were complexed with 5 μl of the reagent in a 100 μl volume of cell culture medium and added to cells after 15 min of incubation. After 24 h, ouabain was added to each well to a final concentration of 10 μM. Cell viability was documented following 24 h incubation.

COS-7 cells (ATCC, Manassas, Va.) were cultured and transfected as above. After 48 h incubation in 10 μM ouabain, the cells were washed twice in PBS (Gibco) and incubated for 15 min in 0.025% porcine trypsine in saline (Sigma). The trypsin was inactivated by FBS addition. The cells were reincubated in 10 µM ouabain. Cell viability was documented following 48 h incubation.

2. Results

2.1 Sub-Cellular Localisation

To monitor the transfection process and sub-cellular localisation of the mutated protein, EGFP-chimeric human/rat $Na^+$, $K^+$-ATPase α1 fusion genes were constructed. Transfection of COS-7 and HeLa cells with pEGFP-chimeric fusion genes resulted in the localization of the fusion protein in the cell membrane. pEGFPR was used as a positive control in the transfection experiments. pEGFPH expression did not confer ouabain resistance on COS-7 cells. Moreover, over-expression of the human $Na^+$, $K^+$-ATPase α1 gene naturally expressed in HeLa by transfection of pEGFPH did not influence ouabain sensitivity. The controls, pEGFPR, pEGFPH, as well as the chimeric EGFP fusion proteins were localised in the cell membrane and detectable by GFP fluorescence. Post-translational regulation of $Na^+$, $K^+$-ATPase α1 expression is controlled by the levels of its cognate β subunit. In transfected cells, the plasmid-encoded protein is competing with the endogenous α subunit for the β subunit and unassembled α-subunits are rapidly degraded (Shanbaky and Pressley, *Biochem. Cell Biol.*, 1995, 73:261-268).

2.2 Ouabain Sensitivity

Sensitivity of the transfected chimeric cDNA to ouabain toxicity was measured in vitro. 10 µM of ouabain induces cell death of wild type HeLa and COS-7, while the rat OuaR construct confers resistance to ouabain and rescues HeLa and COS-7 expressing this α1-subunit. Cell viability of transfected HeLa was documented after 24 h incubation in ouabain. Cell viability of transfected COS-7 was documented after 48 h incubation, followed by trypsination and another 48 h of 10 µM ouabain exposure. Cells transfected with chimeric cDNA with the 5'-end of the chimeric cDNA of rat sequence were resistant to 10 µM ouabain whereas cells transfected with constructs with the 5'-end of human sequence were killed by ouabain induced cell death (FIG. 1), regardless of the constitution the remaining parts of the cDNA. The positive control (pEGFPR) conferred resistance to the transfected cells while the negative control (pEGFPH) and untransduced cells were eliminated by the ouabain exposure. Therefore, the amino acids critical for the 10 µM ouabain-resistant phenotype are situated in the amino terminal of the chimeric α1-subunit, more precisely within the first 129 amino acids. The ouabain-binding site is assumed to be close to the membrane on the extracellular surface. Thus, the present inventors believe the amino acids within and flanking the H1-H2 junction to be of particular importance for the 10 µM ouabain resistance-phenotype of the rat-human chimeric α1-subunit protein.

Experimental Part Added During the Priority Year

3. Materials and Methods

3.1 Site Directed Mutagenesis pEGFPH was used as template to make H-Q118R, H-Q118R; A119S, H-Q126P; N129D, H-N129D. The following primers were used to make overlapping segments, which were joined and amplified by PCR:

```
                                        (SEQ ID NO 15)
TTGTTTCTTGGCTTATAGTATCCGAGCTGCTACAGAAGAGGAACCT
(Q118R forward)

(SEQ ID NO 16)
AGGTTCCTCTTCTGTAGCAGCTCGGATACTATAAGCCAAGAAACAA
(Q118R reverse)

(SEQ ID NO 17)
TTGTTTCTTGGCTTATAGTATCCGATCAGCTACAGAAGAGGAACCT
(Q118R;A119S forward)

(SEQ ID NO 18)
AGGTTCCTCTTCTGTAGCTGATCGGATACTATAAGCCAAGAA ACAA
(Q118R;A119S reverse)

(SEQ ID NO 19)
AGAAGAGGAACCTCCAAACGATGATCTGTACCTGGG
(Q126P;N129D forward)

(SEQ ID NO 20)
CCCAGGTACAGATCATCGTTTGGAGGTTCCTCTTCT
(Q126P;N129D reverse)

(SEQ ID NO 21)
AGAAGAGGAACCTCAAAACGATGATCTGTACCTGGG
(N129D forward)

(SEQ ID NO 22)
CCCAGGTACAGATCATCGTTTTGAGGTTCCTCTTCT
(N129D reverse)
```

The above cDNAs coding for one or two amino acid substitution were used as templates to make H(Q118R; A119S; Q126P; N129D), H(Q118R; Q126P; N129D), H(Q118R; N129D) and H(Q118R; A119S; N129D) and again using the above primers. These constructs were cloned into TOPO vectors (Invitrogen) as described for chimeric cDNAs. An Acc I excised fragment of the clones, containing the mutated region, were inserted into and substituting an Acc I cut pEGFPH. The final cDNAs were as follows; pEGFPH-Q118R; A119S; Q126P; N129D, pEGFPH-Q118R; Q126P; N129D, pEGFPH-Q118R; N129D, pEGFPH-Q118R; A119S; N129D pEGFPH-Q118R pEGFPH-Q118R; A119S pEGFPH-Q126P; N129D pEGFPH-N129D. These constructs were amplified by transformation and prepared as described for chimeric cDNAs. Restriction enzyme mapping and partial sequencing confirmed mutated cDNAs.

3.2 Cell Line

Human epithelial carcinoma HeLa (ATCC, Manassas, Va., USA), Phoenix GP (lymphoblast C1R-sB7) obtained from ATCC with permission from Dr. G Nolan at Dept. of Molecular Pharmacology, Stanford University Medical Center, Stanford, Calif., USA) and mouse retrovirus producer cell line PG13 carrying the GaLV envelope, were cultured in Dulbecco's modified minimal essential medium (DMEM) Glutamax-1 and 10% heat inactivated fetal calf serum (Gibco). For propagation cells were washed twice in PBS (Gibco) and incubated for about 5 min in 0.025% porcine trypsine in saline (Sigma). The trypsine was inactivated by addition of FBS.

3.3 DNA Transfection and Ouabain Toxicity Assay

For transfections, Fugene 6 reagent (Roche Boeringer Mannheim, Germany) was used according to the manufacturer's instructions. Briefly, 2 µg of plasmid DNA per $10^5$ cells were complexed with 5 µl of the reagent in a 100 µl volume of cell culture medium DMEM Glutamax and added to cells after 15 min of incubation. Ouabain (Sigma, St. Louis, Mo., USA) was dissolved in DMEM as a stock solution of 10 mM. For selection experiments 10-500 µM was used. Ouabain was added to the cells at 24 h after transfection. At 48 hours post transfection the cells were trypsinized and transferred to ouabain-free medium. Cell survival was quantified spectrophoto-metrically using the WST-1 cell proliferation reagent (Roche) according to the manufacturer's instructions.

3.4 Retrovirus Vector Construct pMP91$_{MCS}$ was made by inserting the 700 bp Nhe I; Xho I 3'-LTR fragment from pMP71-EGFP containing a multiple cloning site was inserted in the Xba I site in SF91$_{MCS}$. The retrovirus vector pMP91-H(Q118R; N129D) was made as a 3-point DNA ligation of the vector pMP91$_{MCS}$ cut with Hind III and Sal I, a Hind III; Bgl II fragment of the pGC1-H (Q118R; N129D) and a Bgl II; Sal I fragment from pGC3-R1$^{st}$H (containing a PCR introduced Hind III site downstream of the stop codon).

3.5 Production of Viral Supernatant

Recombinant retrovirus vectors were produced by transient transfection of Phoenix GP. Cells were plated at a concentration of 100000 in a 6-well plate. The next day cells were transfected with 3.75 µg of vector plasmid and 0.75 µg of pMDG (provided by D. Trono, Dept of Genetics and microbiology, University of Geneva, Geneva, Switzerland) encoding the vesicular stomatitis virus glycoprotein (VSV-G) using Fugene 6 reagent following the above protocol. 48 hours after transfection the supernatant was collected, filtered and frozen in aliquots at −70° C. The VSV-G pseudotyped retroviral vectors were used to produce PG13 GALV-pseudotype producer cell pools. PG13 cells were plated at a number of about 23000 in a 6-well plate and transduced using 1 ml of the VSV-G. Polybrene was used at a concentration of 4-8 µg/ml. Six rounds of transductions were performed on six consecutive days. The producer cell pools were expanded and used to produce supernatants. Supernatant was collected, filtered through 0.45 µm filters and frozen.

3.6 Transduction and Selection of HeLa

HeLa were seeded to a 6-well plate at a density of $10^5$ per well. 200 µl of frozen pMP91-H(Q118R; N129D) supernatant collected form the PG13 producer cell pool about 5000 TU/ml was warmed to 37° C. and added to the cells. Also, 8 µg/ml of polybrene was added. At 24 hours post transduction ouabain was added to the culture at a concentration of 10 µM. After 48 hours of ouabain selection, cells were washed twice in PBS. Then transduced and selected cells were propagated in ouabain-free medium.

4. Results 4.1 Engineered Resistance of the Human Protein to Ouabain

The present inventors set out to determine the critical amino acids contributing to increased ouabain resistance of the chimeric rat-human Na$^+$, K$^+$-ATPase α1 cDNA. The ouabain binding site is assumed to be close to the membrane on the extracellular surface. Therefore the inventors postulated that the amino acids within and adjacent to the H1-H2 junction would be of particular importance for the 10 µM ouabain resistance-phenotype. Since four positions within the H1-H2 junction (position #118-129, human amino acid sequence) differ between human and rat α1 subunit sequence, the inventors assumed these positions Q118, A119, Q126, and N129 to be critical for the ouabain resistance of the chimeric rat-human Na$^+$, K$^+$-ATPase α1 cDNA. Substituting the amino acids at these positions; human to rat Q118R, A119S, Q126P, N129D in the human cDNA, it could be assessed if, and if so, which of these were required and sufficient to increase resistance of the recombinant human Na$^+$, K$^+$-ATPase α1 subunit to 10 µM ouabain. Amino acid substitutions were made by site directed mutagenesis using PCR techniques. The mutant genes were H-Q118R; A119S; Q126P; N129D, H-Q 118R; A119S; Q126P, H-Q118R; A119S, H-Q126P; N129D, H-Q118R; N129D, H-Q118R, and H-N129D. The mutated human cDNAs were fused in frame with EGFP in the GC1 plasmid using the method described for the chimeric cDNAs.

4.2 Transfection and Selection of Human Cell Lines

Figure 2:
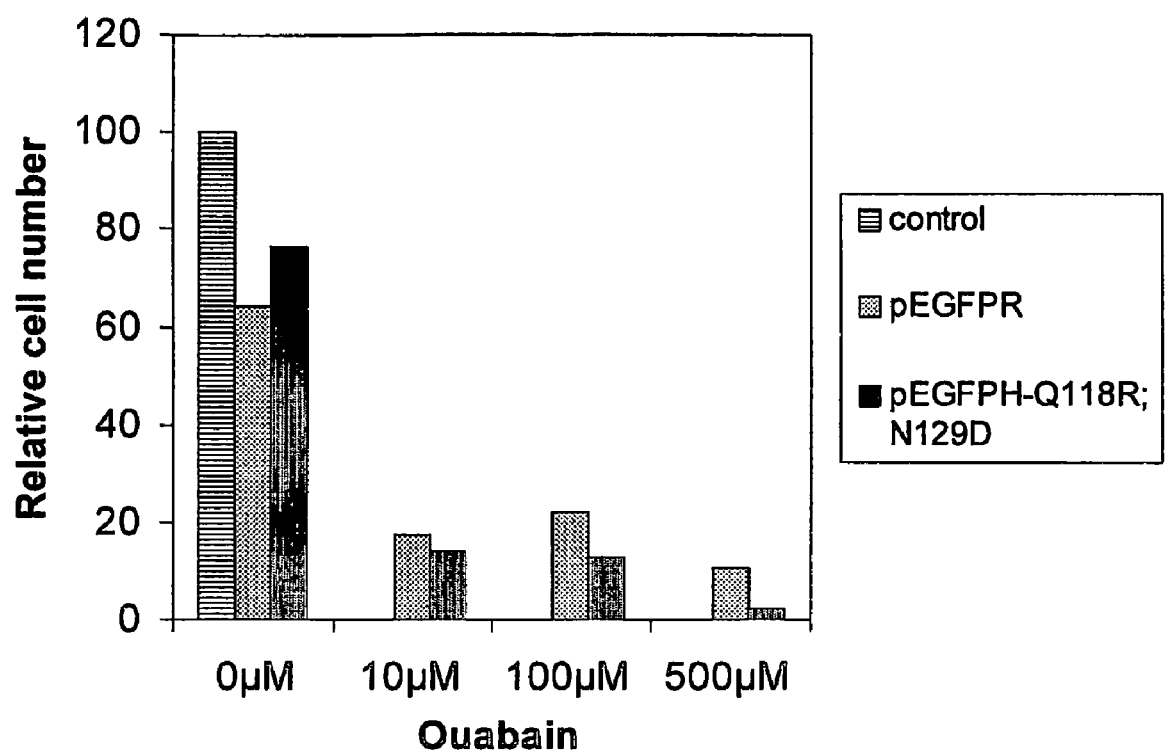
FIG. 2 shows graphically the results of selection of HeLa cells with ouabain after transient transfection. Ouabain was added to the cells 24 hours post transfection. 48 h after transfection cells were trypsinized and transferred to ouabain free medium. The next day cells were washed with PBS and analyzed using WST-1 cell proliferation reagent. Cells were either un-transfected (control), or transfected with the C1 plasmid coding for the EGFP in frame with rat OuaR (pEG-FPR) or with human $Na^+$, $K^+$-ATPase $\alpha 1$ cDNA carrying amino acid substitutions Q118R, N129D (pEGFP-Q118R; N129D).

HeLa cells were transfected with plasmids carrying the EGFP-mutated human cDNAs followed by 24 hours incubation in 10 µM ouabain 24 h post transfection. The mutated genes H-Q118R; A119S; Q126P; N129D, H-Q118R; A119S; Q126P, and H-Q118R; N129D conferred resistance to ouabain, but H-Q118R; A119S, H-Q126P; N129D, H-Q118R, and H-N129D did not. In conclusion, substitutions at two positions; Q118R and N129D, were required and sufficient to confer resistance to 10 µM ouabain of the human Na$^+$, K$^+$-ATPase α1. To determine to what level the minimally mutated human Na$^+$, K$^+$-ATPase α1 conferred ouabain resistance, a dose response assay was performed. HeLa cells were transiently transfected with the plasmid pEGFPH-Q118R; N129D, or pEGFPR. At 24 h the cells expressed sufficient amount of the fusion gene to be selected with ouabain. The transfected cells were selected in various concentration of ouabain (10-500 µM) for 24 hours, then transferred to ouabain-free medium and quantified using the WST-1 proliferation agent. The results are represented in FIG. 2. Control and un-transfected cells were eliminated after 24 hours of ouabain while cells transfected with either the rat OuaR or the human Q118R; N129D substituted Na$^+$, K$^+$-ATPase α1 cDNAs were rescued at 10 and 100 µM ouabain concentrations. 500 µM ouabain was toxic to cells transfected with the mutated human construct and also exhibited some general toxicity to cells transfected with the rat OuaR. Cell debris and cells detached during the ouabain selection were washed and transferred to ouabain-free medium. No surviving cells were observed from detached cells and debris (data not shown).

4.3 Retrovirus Vector Production and Gene Transfer

Using MP91H-Q118R; N129D retrovirus producer cell pools of PG13 we were able to transduce the H-Q118R; N129D cDNA into target HeLa cells. The multiplicity of infection (MOI) was <0.05. Therefore, transduced cells were extremely unlikely to have integrated more than one retrovirus copy per cell. To obtain a pure population of transduced cells, 10 µM ouabain was added 24 h post-transduction for 48 h. The selected cell population was further expanded and propagated in ouabain-free growth medium. Transient transfection with plasmid DNA transfers up to thousands of gene copies per cell resulting in a high transgene expression. In this experiment it was found that only one gene copy expresses the H-Q118R; N129D cDNA in sufficient amounts to confer resistance to 10 µM ouabain.

Although the invention has been described with regard to its preferred embodiments, which constitute the best mode presently known to the inventors, it should be understood that various changes and modifications would be obvious to one having the ordinary skill in the art and may be made without departing from the scope of the invention as set forth in the claims appended hereto.

The invention claimed is:

1. An isolated cell comprising a nucleic acid construct encoding a polypeptide wherein:
   the polypeptide has an amino acid sequence that is at least 98% homologous to an α1-subunit of human Na+, K+ATPase having SEQ ID NO. 1; and
   the polypeptide differs from SEQ ID NO. 1 with respect to at least one amino acid in an amino acid region consisting of amino acids 117-133 of SEQ ID NO. 1, wherein said isolated cell has increased cardiac glycoside resistance compared to an unmodified cell.

2. The cell according to claim 1, wherein the cell is a eukaryotic cell.

3. The cell according to claim 1, wherein the cell is a human cell.

4. The cell according to claim 3, wherein the cell is:
   obtained from a donor or a patient; and
   selected from the group consisting of a primary human cell, a human tumor cell, a cell from a stable human cell line and a human chimeric cell.

5. The cell according to claim 1, wherein the at least one amino acid difference has a maximum of 10 amino acid differences in the amino acid region consisting of amino acids 117-133 of SEQ ID NO. 1.

6. The cell according to claim 1, wherein the at least one amino acid difference has a maximum of 4 amino acid differences in the amino acid region consisting of amino acids 117-133 of SEQ ID NO. 1.

7. The cell according to claim 1, wherein the cell is a partially synthetic cell or a completely synthetic cell.

8. The cell according to claim 1, wherein the difference in at least one amino acid is a difference in at least two amino acids.

9. The cell according to claim 8, wherein the difference in at least two amino acids comprises 2 amino acid substitutions at positions corresponding to Q118R and N129D of SEQ ID NO. 1.

10. The cell according to claim 9, wherein the polypeptide has an amino acid sequence consisting of SEQ ID NO. 23.

11. The cell according to claim 9, wherein the nucleic acid construct has a nucleic acid sequence consisting of SEQ ID NO. 24.

12. The cell according to claim 9, wherein the difference in at least two amino acids is a difference in at least four amino acids.

13. The cell according to claim 12, wherein the polypeptide has an amino acid sequence consisting of SEQ ID NO. 2.

14. The cell according to claim 12, wherein the nucleic acid construct has a nucleic acid sequence consisting of SEQ ID NO. 3.

15. The cell according to claim 9, wherein the polypeptide exhibits increased cardiac glycoside resistance compared to an α1 subunit of $Na^+$, $K^+$ ATPase having SEQ ID NO: 1.

16. The cell according to claim 15, wherein the cell is resistant to a cardiac glycoside selected from the group consisting of ouabain, digoxin, digitoxin, proscillaridine A, palytoxin and convallatoxin.

17. The cell according to claim 16, wherein the cell is resistant to the cardiac glycoside ouabain.

18. The cell according to claim 17, wherein the cell is resistant to at least $10^{-7}$M ouabain.

19. The cell according to claim 1, wherein the nucleic acid construct is introduced into the cell by a method selected from the group consisting of electroporation, transfection, and viral transduction.

20. The cell according to claim 19, wherein the nucleic acid construct is introduced into the cell by viral transduction.

21. The cell according to claim 1, wherein the nucleic acid construct is introduced into the cell by a carrier selected from a group consisting of an exosome, a liposome, and a functional equivalent thereof.

22. The cell according to claim 21, wherein the nucleic acid construct is introduced into the cell by a liposome carrier.

23. The cell according to claim 19, wherein the polypeptide has an amino acid sequence that consists of SEQ ID NO. 23.

24. The cell according to claim 19, wherein the polypeptide has an amino acid sequence that consists of SEQ ID NO. 2.

25. The cell according to claim 19, wherein the cell is a eukaryotic cell.

26. The cell according to claim 19, wherein the cell is a human cell.

27. The cell according to claim 26, wherein the cell is:
obtained from a donor or a patient; and
selected from the group consisting of a primary human cell, a human tumor cell, a cell from a stable human cell line and a human chimeric cell.

28. The cell according to claim 19, wherein the cell is a partially synthetic cell or a completely synthetic cell.

29. The cell according to claim 21, wherein the nucleic acid construct is introduced into the cell by a liposome carrier.

30. The cell according to claim 21, wherein the polypeptide has an amino acid sequence that consists of SEQ ID NO. 23.

31. The cell according to claim 21, wherein the polypeptide has an amino acid sequence that consists of SEQ ID NO. 2.

32. The cell according to claim 21, wherein the cell is a eukaryotic cell.

33. The cell according to claim 21, wherein the cell is a human cell.

34. The cell according to claim 33, wherein the cell is:
obtained from a donor or a patient; and
selected from the group consisting of a primary human cell, a human tumor cell, a cell from a stable human cell line and a human chimeric cell.

35. The cell according to claim 21, wherein the cell is a partially synthetic cell or a completely synthetic cell.

* * * * *

UNITED STATES PATENT AND TRADEMARK OFFICE
CERTIFICATE OF CORRECTION

| | | |
|---|---|---|
| PATENT NO. | : 7,645,603 B2 | Page 1 of 1 |
| APPLICATION NO. | : 10/545491 | |
| DATED | : January 12, 2010 | |
| INVENTOR(S) | : Treschow et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 811 days.

Signed and Sealed this

Sixteenth Day of November, 2010

David J. Kappos
*Director of the United States Patent and Trademark Office*

SEQUENCE LISTING

<160> NUMBER OF SEQ ID NOS: 24

<210> SEQ ID NO 1
<211> LENGTH: 1023
<212> TYPE: PRT
<213> ORGANISM: Homo sapiens
<220> FEATURE:
<221> NAME/KEY: CHAIN
<222> LOCATION: (1)..(1023)
<223> OTHER INFORMATION: Amino acid sequence of the human Na+, K+ ATPase
       (Genebank sequence GI 88220)

<400> SEQUENCE: 1

```
Met Gly Lys Gly Val Gly Arg Asp Lys Tyr Glu Pro Ala Ala Val Ser
1               5                   10                  15

Glu Gln Gly Asp Lys Lys Gly Lys Lys Asp Arg Asp Met
            20                  25                  30

Asp Glu Leu Lys Lys Glu Val Ser Met Asp Asp His Lys Leu Ser Leu
        35                  40                  45

Asp Glu Leu His Arg Lys Tyr Gly Thr Asp Leu Ser Arg Gly Leu Thr
    50                  55                  60

Ser Ala Arg Ala Ala Glu Ile Leu Ala Arg Asp Gly Pro Asn Ala Leu
65                  70                  75                  80

Thr Pro Pro Pro Thr Thr Pro Glu Trp Ile Lys Phe Cys Arg Gln Leu
                85                  90                  95

Phe Gly Gly Phe Ser Met Leu Leu Trp Ile Gly Ala Ile Leu Cys Phe
            100                 105                 110

Leu Ala Tyr Ser Ile Gln Ala Ala Thr Glu Glu Glu Pro Gln Asn Asp
        115                 120                 125

Asn Leu Tyr Leu Gly Val Val Leu Ser Ala Val Val Ile Ile Thr Gly
    130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175

Lys Met Ser Ile Asn Ala Glu Glu Val Val Val Gly Asp Leu Val Glu
            180                 185                 190

Val Lys Gly Gly Asp Arg Ile Pro Ala Asp Leu Arg Ile Ile Ser Ala
        195                 200                 205

Asn Gly Cys Lys Val Asp Asn Ser Ser Leu Thr Gly Glu Ser Glu Pro
    210                 215                 220

Gln Thr Arg Ser Pro Asp Phe Thr Asn Glu Asn Pro Leu Glu Thr Arg
225                 230                 235                 240

Asn Ile Ala Phe Phe Ser Thr Asn Cys Val Glu Gly Thr Ala Arg Gly
                245                 250                 255

Ile Val Val Tyr Thr Gly Asp Arg Thr Val Met Gly Arg Ile Ala Thr
            260                 265                 270

Leu Ala Ser Gly Leu Glu Gly Gly Gln Thr Pro Ile Ala Ala Glu Ile
        275                 280                 285

Glu His Phe Ile His Ile Ile Thr Gly Val Ala Val Phe Leu Gly Val
    290                 295                 300

Ser Phe Phe Ile Leu Ser Leu Ile Leu Glu Tyr Thr Trp Leu Glu Ala
305                 310                 315                 320

Val Ile Phe Leu Ile Gly Ile Ile Val Ala Asn Val Pro Glu Gly Leu
                325                 330                 335
```

```
Leu Ala Thr Val Thr Val Cys Leu Thr Leu Thr Ala Lys Arg Met Ala
            340                 345                 350

Arg Lys Asn Cys Leu Val Lys Asn Leu Glu Ala Val Glu Thr Leu Gly
            355                 360                 365

Ser Thr Ser Thr Ile Cys Ser Asp Lys Thr Gly Thr Leu Thr Gln Asn
            370                 375                 380

Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                405                 410                 415

Thr Trp Leu Ala Leu Ser Arg Ile Ala Gly Leu Cys Asn Arg Ala Val
            420                 425                 430

Phe Gln Ala Asn Gln Glu Asn Leu Pro Ile Leu Lys Arg Ala Val Ala
            435                 440                 445

Gly Asp Ala Ser Glu Ser Ala Leu Leu Lys Cys Ile Glu Leu Cys Cys
450                 455                 460

Gly Ser Val Lys Glu Met Arg Glu Arg Tyr Ala Lys Ile Val Glu Ile
465                 470                 475                 480

Pro Phe Asn Ser Thr Asn Lys Tyr Gln Leu Ser Ile His Lys Asn Pro
                485                 490                 495

Asn Thr Ser Glu Pro Gln His Leu Leu Val Met Lys Gly Ala Pro Glu
            500                 505                 510

Arg Ile Leu Asp Arg Cys Ser Ser Ile Leu Leu His Gly Lys Glu Gln
            515                 520                 525

Pro Leu Asp Glu Glu Leu Lys Asp Ala Phe Gln Asn Ala Tyr Leu Glu
            530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Asp Val
                565                 570                 575

Asn Phe Pro Ile Asp Asn Leu Cys Phe Val Gly Leu Ile Ser Met Ile
            580                 585                 590

Asp Pro Pro Arg Ala Ala Val Pro Asp Ala Val Gly Lys Cys Arg Ser
            595                 600                 605

Ala Gly Ile Lys Val Ile Met Val Thr Gly Asp His Pro Ile Thr Ala
            610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Ser Gln Val Asn
                645                 650                 655

Pro Arg Asp Ala Lys Ala Cys Val Val His Gly Ser Asp Leu Lys Asp
            660                 665                 670

Met Thr Ser Glu Gln Leu Asp Asp Ile Leu Lys Tyr His Thr Glu Ile
            675                 680                 685

Val Phe Ala Arg Thr Ser Pro Gln Gln Lys Leu Ile Ile Val Glu Gly
            690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Ala Gly Ser Asp Val Ser Lys Gln Ala Ala Asp Met Ile Leu Leu Asp
            740                 745                 750
```

-continued

```
Asp Asn Phe Ala Ser Ile Val Thr Gly Val Glu Glu Gly Arg Leu Ile
        755                 760                 765
Phe Asp Asn Leu Lys Lys Ser Ile Ala Tyr Thr Leu Thr Ser Asn Ile
770                 775                 780
Pro Glu Ile Thr Pro Phe Leu Ile Phe Ile Ile Ala Asn Ile Pro Leu
785                 790                 795                 800
Pro Leu Gly Thr Val Thr Ile Leu Cys Ile Asp Leu Gly Thr Asp Met
                805                 810                 815
Val Pro Ala Ile Ser Leu Ala Tyr Glu Gln Ala Glu Ser Asp Ile Met
                820                 825                 830
Lys Arg Gln Pro Arg Asn Pro Lys Thr Asp Lys Leu Val Asn Glu Arg
                835                 840                 845
Leu Ile Ser Met Ala Tyr Gly Gln Ile Gly Met Ile Gln Ala Leu Gly
        850                 855                 860
Gly Phe Phe Thr Tyr Phe Val Ile Leu Ala Glu Asn Gly Phe Leu Pro
865                 870                 875                 880
Ile His Leu Leu Gly Leu Arg Val Asp Trp Asp Asp Arg Trp Ile Asn
                885                 890                 895
Asp Val Glu Asp Ser Tyr Gly Gln Gln Trp Thr Tyr Glu Gln Arg Lys
                900                 905                 910
Ile Val Glu Phe Thr Cys His Thr Ala Phe Phe Val Ser Ile Val Val
        915                 920                 925
Val Gln Trp Ala Asp Leu Val Ile Cys Lys Thr Arg Arg Asn Ser Val
        930                 935                 940
Phe Gln Gln Gly Met Lys Asn Lys Ile Leu Ile Phe Gly Leu Phe Glu
945                 950                 955                 960
Glu Thr Ala Leu Ala Ala Phe Leu Ser Tyr Cys Pro Gly Met Gly Val
                965                 970                 975
Ala Leu Arg Met Tyr Pro Leu Lys Pro Thr Trp Trp Phe Cys Ala Phe
                980                 985                 990
Pro Tyr Ser Leu Leu Ile Phe Val Tyr Asp Glu Val Arg Lys Leu Ile
        995                 1000                1005
Ile Arg Arg Arg Pro Gly Gly Trp Val Glu Lys Glu Thr Tyr Tyr
        1010                1015                1020

<210> SEQ ID NO 2
<211> LENGTH: 1023
<212> TYPE: PRT
<213> ORGANISM: Artificial Sequence
<220> FEATURE:
<223> OTHER INFORMATION: Amino acid sequence of recombinant Na+, K+
      ATPase

<400> SEQUENCE: 2

Met Gly Lys Gly Val Gly Arg Asp Lys Tyr Glu Pro Ala Ala Val Ser
1               5                   10                  15
Glu His Gly Asp Lys Lys Ser Lys Lys Ala Lys Lys Glu Arg Asp Met
                20                  25                  30
Asp Glu Leu Lys Lys Glu Val Ser Met Asp Asp His Lys Leu Ser Leu
        35                  40                  45
Asp Glu Leu His Arg Lys Tyr Gly Thr Asp Leu Ser Arg Gly Leu Thr
    50                  55                  60
Pro Ala Arg Ala Ala Glu Ile Leu Ala Arg Asp Gly Pro Asn Ala Leu
65                  70                  75                  80
Thr Pro Pro Pro Thr Thr Pro Glu Trp Val Lys Phe Cys Arg Gln Leu
                85                  90                  95
```

```
Phe Gly Gly Phe Ser Met Leu Leu Trp Ile Gly Ala Ile Leu Cys Phe
                100                 105                 110

Leu Ala Tyr Gly Ile Arg Ser Ala Thr Glu Glu Pro Pro Asn Asp
            115                 120                 125

Asp Leu Tyr Leu Gly Val Val Leu Ser Ala Val Val Ile Ile Thr Gly
        130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175

Lys Met Ser Ile Asn Ala Glu Glu Val Val Gly Asp Leu Val Glu
            180                 185                 190

Val Lys Gly Gly Asp Arg Ile Pro Ala Asp Leu Arg Ile Ile Ser Ala
        195                 200                 205

Asn Gly Cys Lys Val Asp Asn Ser Ser Leu Thr Gly Glu Ser Glu Pro
210                 215                 220

Gln Thr Arg Ser Pro Asp Phe Thr Asn Glu Asn Pro Leu Glu Thr Arg
225                 230                 235                 240

Asn Ile Ala Phe Phe Ser Thr Asn Cys Val Glu Gly Thr Ala Arg Gly
                245                 250                 255

Ile Val Val Tyr Thr Gly Asp Arg Thr Val Met Gly Arg Ile Ala Thr
            260                 265                 270

Leu Ala Ser Gly Leu Glu Gly Gly Gln Thr Pro Ile Ala Ala Glu Ile
        275                 280                 285

Glu His Phe Ile His Ile Ile Thr Gly Val Ala Val Phe Leu Gly Val
290                 295                 300

Ser Phe Phe Ile Leu Ser Leu Ile Leu Glu Tyr Thr Trp Leu Glu Ala
305                 310                 315                 320

Val Ile Phe Leu Ile Gly Ile Ile Val Ala Asn Val Pro Glu Gly Leu
                325                 330                 335

Leu Ala Thr Val Thr Val Cys Leu Thr Leu Thr Ala Lys Arg Met Ala
            340                 345                 350

Arg Lys Asn Cys Leu Val Lys Asn Leu Glu Ala Val Glu Thr Leu Gly
        355                 360                 365

Ser Thr Ser Thr Ile Cys Ser Asp Lys Thr Gly Thr Leu Thr Gln Asn
370                 375                 380

Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                405                 410                 415

Thr Trp Leu Ala Leu Ser Arg Ile Ala Gly Leu Cys Asn Arg Ala Val
            420                 425                 430

Phe Gln Ala Asn Gln Glu Asn Leu Pro Ile Leu Lys Arg Ala Val Ala
        435                 440                 445

Gly Asp Ala Ser Glu Ser Ala Leu Leu Lys Cys Ile Glu Leu Cys Cys
450                 455                 460

Gly Ser Val Lys Glu Met Arg Glu Arg Tyr Ala Lys Ile Val Glu Ile
465                 470                 475                 480

Pro Phe Asn Ser Thr Asn Lys Tyr Gln Leu Ser Ile His Lys Asn Pro
                485                 490                 495

Asn Thr Ser Glu Pro Gln His Leu Leu Val Met Lys Gly Ala Pro Glu
            500                 505                 510
```

-continued

```
Arg Ile Leu Asp Arg Cys Ser Ser Ile Leu His Gly Lys Glu Gln
        515                 520                 525

Pro Leu Asp Glu Glu Leu Lys Asp Ala Phe Gln Asn Ala Tyr Leu Glu
    530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Asp Val
                565                 570                 575

Asn Phe Pro Ile Asp Asn Leu Cys Phe Val Gly Leu Ile Ser Met Ile
            580                 585                 590

Asp Pro Pro Arg Ala Ala Val Pro Asp Ala Val Gly Lys Cys Arg Ser
        595                 600                 605

Ala Gly Ile Lys Val Ile Met Val Thr Gly Asp His Pro Ile Thr Ala
    610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Ser Gln Val Asn
                645                 650                 655

Pro Arg Asp Ala Lys Ala Cys Val Val His Gly Ser Asp Leu Lys Asp
            660                 665                 670

Met Thr Ser Glu Gln Leu Asp Asp Ile Leu Lys Tyr His Thr Glu Ile
        675                 680                 685

Val Phe Ala Arg Thr Ser Pro Gln Gln Lys Leu Ile Ile Val Glu Gly
    690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Ala Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
        755                 760                 765

Phe Asp Asn Leu Lys Lys Ser Ile Ala Tyr Thr Leu Thr Ser Asn Ile
    770                 775                 780

Pro Glu Ile Thr Pro Phe Leu Ile Phe Ile Ile Ala Asn Ile Pro Leu
785                 790                 795                 800

Pro Leu Gly Thr Val Thr Ile Leu Cys Ile Asp Leu Gly Thr Asp Met
                805                 810                 815

Val Pro Ala Ile Ser Leu Ala Tyr Glu Gln Ala Glu Ser Asp Ile Met
            820                 825                 830

Lys Arg Gln Pro Arg Asn Pro Lys Thr Asp Lys Leu Val Asn Glu Arg
        835                 840                 845

Leu Ile Ser Met Ala Tyr Gly Gln Ile Gly Met Ile Gln Ala Leu Gly
    850                 855                 860

Gly Phe Phe Thr Tyr Phe Val Ile Leu Ala Glu Asn Gly Phe Leu Pro
865                 870                 875                 880

Ile His Leu Leu Gly Leu Arg Val Asp Trp Asp Asp Arg Trp Ile Asn
                885                 890                 895

Asp Val Glu Asp Ser Tyr Gly Gln Gln Trp Thr Tyr Glu Gln Arg Lys
            900                 905                 910

Ile Val Glu Phe Thr Cys His Thr Ala Phe Phe Val Ser Ile Val Val
        915                 920                 925

Val Gln Trp Ala Asp Leu Val Ile Cys Lys Thr Arg Arg Asn Ser Val
```

```
                930             935              940
Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Val
                965                 970                 975

Ala Leu Arg Met Tyr Pro Leu Lys Pro Thr Trp Trp Phe Cys Ala Phe
            980                 985                 990

Pro Tyr Ser Leu Leu Ile Phe Val Tyr Asp Glu Val Arg Lys Leu Ile
            995                 1000                1005

Ile Arg Arg Arg Pro Gly Gly  Trp Val Glu Lys Glu  Thr Tyr Tyr
    1010            1015                 1020
```

```
<210> SEQ ID NO 3
<211> LENGTH: 3072
<212> TYPE: DNA
<213> ORGANISM: Artificial Sequence
<220> FEATURE:
<223> OTHER INFORMATION: Nucleic acid sequence encoding the recombinant
      Na+, K+ ATPase

<400> SEQUENCE: 3
atggggaagg gggttggacg agacaagtat gagcccgcag ctgtatcaga acatggggac     60
aagaagagca agaaggcgaa gaaggaaagg gacatggacg aactcaagaa ggaagtgtct    120
atggacgacc ataaactcag cctggatgaa ctccatcgta atacggaac agatttgagc     180
cgaggcctaa caccccgcaag ggccgctgag atcctggctc gggatggccc caacgccctc    240
acgccccctc ccactactcc cgagtgggtc aaattctgtc ggcagctgtt cggtggcttc    300
tccatgttac tgtggattgg agccattctt gtttcttgg cttatggcat ccgaagtgct     360
acagaagagg aaccaccaaa tgatgatctg tacctgggtg tggtgctatc agccgttgta    420
atcataactg gttgcttctc ctactatcaa gaagctaaaa gttcaaagat catggaatcc    480
ttcaaaaaca tggtccctca gcaagccctt gtgattcgaa atggtgagaa atgagcata    540
aatgcggaga agttgtggt tggggatctg gtggaagtaa aaggaggaga ccgaattcct    600
gctgacctca gaatcatatc tgcaaatggc tgcaaggtgg ataactcctc gctcactggt    660
gaatcagaac cccagactag gtctccagat ttcacaaatg aaaaccccct ggagacgagg    720
aacattgcct tcttttcaac aaaattgtgtt gaaggcaccg cacgtggtat tgttgtctac    780
actggggatc gcactgtgat gggaagaatt gccacacttg cttctgggct ggaaggaggc    840
cagaccccca ttgctgcaga aattgaacat tttatccaca tcatcacggg tgtggctgtg    900
ttcctgggtg tgtctttctt catcctttct ctcatccttg agtacacctg gcttgaggct    960
gtcatcttcc tcatcggtat catcgtagcc aatgtgccgg aaggtttgct ggccactgtc   1020
acggtctgtc tgacacttac tgccaaacgc atggcaagga aaaactgctt agtgaagaac   1080
ttagaagctg tggagacctt gggggtccacg tccaccatct gctctgataa actggaact    1140
ctgactcaga accggatgac agtggcccac atgtggtttg acaatcaaat ccatgaagct   1200
gatacgacag agaatcagag tggtgtctct tttgacaaga cttcagctac ctggcttgct   1260
ctgtccagaa ttgcaggtct ttgtaacagg gcagtgtttc aggctaacca ggaaaaccta   1320
cctattctta gcgggcagt tgcaggagat gcctctgagt cagcactctt aaagtgcata   1380
gagctgtgct gtggttccgt gaaggagatg agagaaagat acgccaaaat cgtcgagata   1440
cccttcaact ccaccaacaa gtaccagttg tctattcata agaaccccaa acatcggag    1500
ccccaacacc tgttggtgat gaagggcgcc ccagaaagga tcctagaccg ttgcagctct   1560
```

```
atcctcctcc acggcaagga gcagccctg gatgaggagc tgaaagacgc ctttcagaac      1620
gcctatttgg agctgggggg cctcggagaa cgagtcctag gtttctgcca cctctttctg     1680
ccagatgaac agtttcctga agggttccag tttgacactg acgatgtgaa tttccctatc     1740
gataatctgt gctttgttgg gctcatctcc atgattgacc ctccacgggc ggccgttcct     1800
gatgccgtgg gcaaatgtcg aagtgctgga attaaggtca tcatggtcac aggagaccat     1860
ccaatcacag ctaaagctat tgccaaaggt gtgggcatca tctcagaagg caatgagacc     1920
gtggaagaca ttgctgcccg cctcaacatc ccagtcagcc aggtgaaccc cagggatgcc     1980
aaggcctgcg tagtacacgg cagtgatcta aaggacatga cctccgagca gctggatgac     2040
attttgaagt accacactga gatagtgttt gccaggacct cccctcagca gaagctcatc     2100
attgtggaag gctgccaaag acagggtgct atcgtggctg tgactggtga cggtgtgaat     2160
gactctccag ctttgaagaa gcagacatt ggggttgcta tggggattgc tggctcagat     2220
gtgtccaagc aagctgctga catgattctt ctggatgaca actttgcctc aattgtgact     2280
ggagtagagg aaggtcgtct gatctttgat aacttgaaga atccattgc ttataccttta    2340 accagtaaca ttcccgagat caccccgttc ctgatattta ttattgcaaa cattccacta     2400
ccactgggga ctgtcaccat cctctgcatt gacttgggca ctgacatggt tcctgccatc     2460
tccctggctt atgagcaggc tgagagtgac atcatgaaga cagcccag aaatcccaaa       2520 acagacaaac ttgtgaatga gcggctgatc agcatggcct atgggcagat tggaatgatc    2580
caggccctgg gaggcttctt tacttacttt gtgattctgg ctgagaacgg cttcctccca     2640
attcacctgt tgggcctccg agtggactgg gatgaccgct ggatcaacga tgtggaagac    2700
agctacgggg agcagtggac ctatgagcag aggaaaatcg tggagttcac ctgccacaca     2760
gccttcttcg tcagtatcgt ggtggtgcag tgggccgact tggtcatctg taagaccagg     2820
aggaattcgg tcttccagca ggggatgaag aacaagatct tgatatttgg cctcttttgaa   2880 gagacagccc tggctgcttt ccttttcctac tgccctggaa tgggtgttgc tcttaggatg    2940
tatcccctca aacctacctg gtggttctgt gccttcccct actctcttct catcttcgta    3000
tatgacgaag tcagaaaact catcatcagg cgacgccctg gcggctgggt ggagaaggaa    3060
acctactatt ag                                                         3072
```

```
<210> SEQ ID NO 4
<211> LENGTH: 38
<212> TYPE: DNA
<213> ORGANISM: Artificial Sequence
<220> FEATURE:
<223> OTHER INFORMATION: Forward primer

<400> SEQUENCE: 4
ggaacctcaa aacgataatc tgtacctcgg ggtcgtgc                              38

<210> SEQ ID NO 5
<211> LENGTH: 36
<212> TYPE: DNA
<213> ORGANISM: Artificial Sequence
<220> FEATURE:
<223> OTHER INFORMATION: Forward primer

<400> SEQUENCE: 5
tcatcacggg tgtggctgtg ttcctggggg tgtctt                                36

<210> SEQ ID NO 6
```

```
<211> LENGTH: 38
<212> TYPE: DNA
<213> ORGANISM: Artificial Sequence
<220> FEATURE:
<223> OTHER INFORMATION: Reverse primer

<400> SEQUENCE: 6
aagacacacc caggaacaca gccacacccg tgatgagg                              38

<210> SEQ ID NO 7
<211> LENGTH: 39
<212> TYPE: DNA
<213> ORGANISM: Artificial Sequence
<220> FEATURE:
<223> OTHER INFORMATION: Reverse primer

<400> SEQUENCE: 7
agcaccacac ccaggtacag atcatcattt ggtggttcc                             39

<210> SEQ ID NO 8
<211> LENGTH: 19
<212> TYPE: DNA
<213> ORGANISM: Artificial Sequence
<220> FEATURE:
<223> OTHER INFORMATION: Reverse primer

<400> SEQUENCE: 8
ggcaagcttg ttatctaga                                                   19

<210> SEQ ID NO 9
<211> LENGTH: 39
<212> TYPE: DNA
<213> ORGANISM: Artificial Sequence
<220> FEATURE:
<223> OTHER INFORMATION: Forward primer

<400> SEQUENCE: 9
ggaaccacca aatgatgatc tgtacctggg tgtggtgct                             39

<210> SEQ ID NO 10
<211> LENGTH: 38
<212> TYPE: DNA
<213> ORGANISM: Artificial Sequence
<220> FEATURE:
<223> OTHER INFORMATION: Forward primer

<400> SEQUENCE: 10
cctcatcacg ggtgtggctg tgttcctggg tgtgtctt                              38

<210> SEQ ID NO 11
<211> LENGTH: 38
<212> TYPE: DNA
<213> ORGANISM: Artificial Sequence
<220> FEATURE:
<223> OTHER INFORMATION: Forward primer

<400> SEQUENCE: 11
gcacgacccc gaggtacaga ttatcgtttt gaggttcc                              38

<210> SEQ ID NO 12
<211> LENGTH: 36
<212> TYPE: DNA
<213> ORGANISM: Artificial Sequence
<220> FEATURE:
<223> OTHER INFORMATION: Reverse primer

<400> SEQUENCE: 12
```
aagacacccc caggaacaca gccacacccg tgatga                          36

<210> SEQ ID NO 13
<211> LENGTH: 30
<212> TYPE: DNA
<213> ORGANISM: Artificial Sequence
<220> FEATURE:
<223> OTHER INFORMATION: Reverse primer

<400> SEQUENCE: 13
gcgaagcttg acgggggggct aatagtaggt                                30

<210> SEQ ID NO 14
<211> LENGTH: 22
<212> TYPE: DNA
<213> ORGANISM: Artificial Sequence
<220> FEATURE:
<223> OTHER INFORMATION: Forward primer

<400> SEQUENCE: 14
cgggatcact ctcggcatgg ac                                         22

<210> SEQ ID NO 15
<211> LENGTH: 46
<212> TYPE: DNA
<213> ORGANISM: Artificial Sequence
<220> FEATURE:
<223> OTHER INFORMATION: Q118R Forward primer

<400> SEQUENCE: 15
ttgtttcttg gcttatagta tccgagctgc tacagaagag gaacct               46

<210> SEQ ID NO 16
<211> LENGTH: 46
<212> TYPE: DNA
<213> ORGANISM: Artificial Sequence
<220> FEATURE:
<223> OTHER INFORMATION: Q188R Reverse primer

<400> SEQUENCE: 16
aggttcctct tctgtagcag ctcggatact ataagccaag aaacaa               46

<210> SEQ ID NO 17
<211> LENGTH: 46
<212> TYPE: DNA
<213> ORGANISM: Artificial Sequence
<220> FEATURE:
<223> OTHER INFORMATION: Q118R; A119S Forward primer

<400> SEQUENCE: 17
ttgtttcttg gcttatagta tccgatcagc tacagaagag gaacct               46

<210> SEQ ID NO 18
<211> LENGTH: 46
<212> TYPE: DNA
<213> ORGANISM: Artificial Sequence
<220> FEATURE:
<223> OTHER INFORMATION: Q118R; A119S Reverse primer

<400> SEQUENCE: 18
aggttcctct tctgtagctg atcggatact ataagccaag aaacaa               46

<210> SEQ ID NO 19
<211> LENGTH: 36
<212> TYPE: DNA

<210> SEQ ID NO 19
<211> LENGTH: 36
<212> TYPE: DNA
<213> ORGANISM: Artificial Sequence
<220> FEATURE:
<223> OTHER INFORMATION: Q126P; N129D Forward primer

<400> SEQUENCE: 19
agaagaggaa cctccaaacg atgatctgta cctggg    36

<210> SEQ ID NO 20
<211> LENGTH: 36
<212> TYPE: DNA
<213> ORGANISM: Artificial Sequence
<220> FEATURE:
<223> OTHER INFORMATION: Q126P; N129D Reverse primer

<400> SEQUENCE: 20
cccaggtaca gatcatcgtt tggaggttcc tcttct    36

<210> SEQ ID NO 21
<211> LENGTH: 36
<212> TYPE: DNA
<213> ORGANISM: Artificial Sequence
<220> FEATURE:
<223> OTHER INFORMATION: N129D Forward primer

<400> SEQUENCE: 21
agaagaggaa cctcaaaacg atgatctgta cctggg    36

<210> SEQ ID NO 22
<211> LENGTH: 36
<212> TYPE: DNA
<213> ORGANISM: Artificial Sequence
<220> FEATURE:
<223> OTHER INFORMATION: N129D Reverse primer

<400> SEQUENCE: 22
cccaggtaca gatcatcgtt ttgaggttcc tcttct    36

<210> SEQ ID NO 23
<211> LENGTH: 1023
<212> TYPE: PRT
<213> ORGANISM: Artificial Sequence
<220> FEATURE:
<223> OTHER INFORMATION: 2 amino acid substituted sequence of Na+,K+ ATPase subunit alpha1

<400> SEQUENCE: 23

```
Met Gly Lys Gly Val Gly Arg Asp Lys Tyr Glu Pro Ala Ala Val Ser
1               5                   10                  15

Glu Gln Gly Asp Lys Lys Gly Lys Lys Gly Lys Lys Asp Arg Asp Met
            20                  25                  30

Asp Glu Leu Lys Lys Glu Val Ser Met Asp Asp His Lys Leu Ser Leu
        35                  40                  45

Asp Glu Leu His Arg Lys Tyr Gly Thr Asp Leu Ser Arg Gly Leu Thr
    50                  55                  60

Ser Ala Arg Ala Ala Glu Ile Leu Ala Arg Asp Gly Pro Asn Ala Leu
65                  70                  75                  80

Thr Pro Pro Pro Thr Thr Pro Glu Trp Ile Lys Phe Cys Arg Gln Leu
                85                  90                  95

Phe Gly Gly Phe Ser Met Leu Leu Trp Ile Gly Ala Ile Leu Cys Phe
            100                 105                 110

Leu Ala Tyr Ser Ile Arg Ala Ala Thr Glu Glu Glu Pro Gln Asn Asp
        115                 120                 125
```

-continued

```
Asp Leu Tyr Leu Gly Val Val Leu Ser Ala Val Val Ile Thr Gly
    130                 135                 140
Cys Phe Ser Tyr Tyr Gln Glu Ala Lys Ser Ser Lys Ile Met Glu Ser
145                 150                 155                 160
Phe Lys Asn Met Val Pro Gln Gln Ala Leu Val Ile Arg Asn Gly Glu
                165                 170                 175
Lys Met Ser Ile Asn Ala Glu Glu Val Val Gly Asp Leu Val Glu
                180                 185                 190
Val Lys Gly Gly Asp Arg Ile Pro Ala Asp Leu Arg Ile Ile Ser Ala
            195                 200                 205
Asn Gly Cys Lys Val Asp Asn Ser Ser Leu Thr Gly Glu Ser Glu Pro
    210                 215                 220
Gln Thr Arg Ser Pro Asp Phe Thr Asn Glu Asn Pro Leu Glu Thr Arg
225                 230                 235                 240
Asn Ile Ala Phe Phe Ser Thr Asn Cys Val Glu Gly Thr Ala Arg Gly
                245                 250                 255
Ile Val Val Tyr Thr Gly Asp Arg Thr Val Met Gly Arg Ile Ala Thr
                260                 265                 270
Leu Ala Ser Gly Leu Glu Gly Gly Gln Thr Pro Ile Ala Ala Glu Ile
            275                 280                 285
Glu His Phe Ile His Ile Ile Thr Gly Val Ala Val Phe Leu Gly Val
    290                 295                 300
Ser Phe Phe Ile Leu Ser Leu Ile Leu Glu Tyr Thr Trp Leu Glu Ala
305                 310                 315                 320
Val Ile Phe Leu Ile Gly Ile Ile Val Ala Asn Val Pro Glu Gly Leu
                325                 330                 335
Leu Ala Thr Val Thr Val Cys Leu Thr Leu Thr Ala Lys Arg Met Ala
            340                 345                 350
Arg Lys Asn Cys Leu Val Lys Asn Leu Glu Ala Val Glu Thr Leu Gly
    355                 360                 365
Ser Thr Ser Thr Ile Cys Ser Asp Lys Thr Gly Thr Leu Thr Gln Asn
    370                 375                 380
Arg Met Thr Val Ala His Met Trp Phe Asp Asn Gln Ile His Glu Ala
385                 390                 395                 400
Asp Thr Thr Glu Asn Gln Ser Gly Val Ser Phe Asp Lys Thr Ser Ala
                405                 410                 415
Thr Trp Leu Ala Leu Ser Arg Ile Ala Gly Leu Cys Asn Arg Ala Val
            420                 425                 430
Phe Gln Ala Asn Gln Glu Asn Leu Pro Ile Leu Lys Arg Ala Val Ala
    435                 440                 445
Gly Asp Ala Ser Glu Ser Ala Leu Leu Lys Cys Ile Glu Leu Cys Cys
    450                 455                 460
Gly Ser Val Lys Glu Met Arg Glu Arg Tyr Ala Lys Ile Val Glu Ile
465                 470                 475                 480
Pro Phe Asn Ser Thr Asn Lys Tyr Gln Leu Ser Ile His Lys Asn Pro
                485                 490                 495
Asn Thr Ser Glu Pro Gln His Leu Leu Val Met Lys Gly Ala Pro Glu
            500                 505                 510
Arg Ile Leu Asp Arg Cys Ser Ser Ile Leu Leu His Gly Lys Glu Gln
    515                 520                 525
Pro Leu Asp Glu Glu Leu Lys Asp Ala Phe Gln Asn Ala Tyr Leu Glu
    530                 535                 540
Leu Gly Gly Leu Gly Glu Arg Val Leu Gly Phe Cys His Leu Phe Leu
```

```
                                     -continued
545                 550                 555                 560

Pro Asp Glu Gln Phe Pro Glu Gly Phe Gln Phe Asp Thr Asp Asp Val
                565                 570                 575

Asn Phe Pro Ile Asp Asn Leu Cys Phe Val Gly Leu Ile Ser Met Ile
                580                 585                 590

Asp Pro Pro Arg Ala Ala Val Pro Asp Ala Val Gly Lys Cys Arg Ser
                595                 600                 605

Ala Gly Ile Lys Val Ile Met Val Thr Gly Asp His Pro Ile Thr Ala
            610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Ser Gln Val Asn
                645                 650                 655

Pro Arg Asp Ala Lys Ala Cys Val Val His Gly Ser Asp Leu Lys Asp
                660                 665                 670

Met Thr Ser Glu Gln Leu Asp Asp Ile Leu Lys Tyr His Thr Glu Ile
            675                 680                 685

Val Phe Ala Arg Thr Ser Pro Gln Gln Lys Leu Ile Ile Val Glu Gly
        690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Ala Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
        755                 760                 765

Phe Asp Asn Leu Lys Lys Ser Ile Ala Tyr Thr Leu Thr Ser Asn Ile
    770                 775                 780

Pro Glu Ile Thr Pro Phe Leu Ile Phe Ile Ile Ala Asn Ile Pro Leu
785                 790                 795                 800

Pro Leu Gly Thr Val Thr Ile Leu Cys Ile Asp Leu Gly Thr Asp Met
                805                 810                 815

Val Pro Ala Ile Ser Leu Ala Tyr Glu Gln Ala Glu Ser Asp Ile Met
            820                 825                 830

Lys Arg Gln Pro Arg Asn Pro Lys Thr Asp Lys Leu Val Asn Glu Arg
        835                 840                 845

Leu Ile Ser Met Ala Tyr Gly Gln Ile Gly Met Ile Gln Ala Leu Gly
    850                 855                 860

Gly Phe Phe Thr Tyr Phe Val Ile Leu Ala Glu Asn Gly Phe Leu Pro
865                 870                 875                 880

Ile His Leu Leu Gly Leu Arg Val Asp Trp Asp Asp Arg Trp Ile Asn
                885                 890                 895

Asp Val Glu Asp Ser Tyr Gly Gln Gln Trp Thr Tyr Glu Gln Arg Lys
            900                 905                 910

Ile Val Glu Phe Thr Cys His Thr Ala Phe Phe Val Ser Ile Val Val
        915                 920                 925

Val Gln Trp Ala Asp Leu Val Ile Cys Lys Thr Arg Arg Asn Ser Val
    930                 935                 940

Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Val
                965                 970                 975
```

```
Ala Leu Arg Met Tyr Pro Leu Lys Pro Thr Trp Trp Phe Cys Ala Phe
            980                 985                 990

Pro Tyr Ser Leu Leu Ile Phe Val  Tyr Asp Glu Val Arg  Lys Leu Ile
            995                 1000                1005

Ile Arg  Arg Arg Pro Gly Gly  Trp Val Glu Lys Glu  Thr Tyr Tyr
     1010                1015                 1020

<210> SEQ ID NO 24
<211> LENGTH: 3072
<212> TYPE: DNA
<213> ORGANISM: Artificial Sequence
<220> FEATURE:
<223> OTHER INFORMATION: Nucleic acid sequence encoding 2 aa substituted
      recombinant Na+,K+ ATPase subunit alpha1

<400> SEQUENCE: 24
atggggaagg gggttggacg tgataagtat gagcctgcag ctgtttcaga acaaggtgat      60
aaaaagggca aaaagggcaa aaaagacagg gacatggatg aactgaagaa agaagtttct    120
atggatgatc ataaacttag ccttgatgaa cttcatcgta aatatggaac agacttgagc    180
cggggattaa catctgctcg tgcagctgag atcctggcgc gagatggtcc caacgccctc    240
actccccctc ccactactcc tgaatggatc aagttttgtc ggcagctctt tgggggttc     300 tcaatgttac tgtggattgg agcgattctt tgtttcttgg cttatagtat ccgagctgct    360
acagaagagg aacctcaaaa cgatgatctg tacctgggtg tggtgctatc agccgttgta    420
atcataactg gttgcttctc ctactatcaa gaagctaaaa gttcaaagat catggaatcc    480
ttcaaaaaca tggtccctca gcaagccctt gtgattcgaa atggtgagaa atgagcata    540 aatgcggagg aagttgtggt tggggatctg gtggaagtaa aggaggaga ccgaattcct    600 gctgacctca gaatcatatc tgcaaatggc tgcaaggtgg ataactcctc gctcactggt    660
gaatcagaac cccagactag gtctccagat ttcacaaatg aaaaccccct ggagacgagg    720
aacattgcct tcttttcaac caattgtgtt gaaggcaccg cacgtggtat tgttgtctac    780
actggggatc gcactgtgat gggaagaatt gccacacttg cttctgggct ggaaggaggc    840
cagaccccca ttgctgcaga aattgaacat tttatccaca tcatcacggg tgtggctgtg    900
ttcctgggtg tgtcttttct catcctttct ctcatccttg agtacacctg gcttgaggct    960
gtcatcttcc tcatcggtat catcgtagcc aatgtgccgg aaggtttgct ggccactgtc   1020
acggtctgtc tgacacttac tgccaaacgc atggcaagga aaactgcttt agtgaagaac   1080
ttagaagctg tggagaccct ggggtccacg tccaccatct gctctgataa aactggaact   1140
ctgactcaga accggatgac agtggcccac atgtggtttg acaatcaaat ccatgaagct   1200
gatacgacag agaatcagag tggtgtctct tttgacaaga cttcagctac ctggcttgct   1260
ctgtccagaa ttgcaggtct ttgtaacagg gcagtgtttc aggctaacca ggaaaaccta   1320
cctattctta agcgggcagt tgcaggagat gcctctgagt cagcactctt aaagtgcata   1380
gagctgtgct gtggttccgt gaaggagatg agagaaagat acgccaaaat cgtcgagata   1440
cccttcaact ccaccaacaa gtaccagttg tctattcata agaaccccaa cacatcggag   1500
ccccaacacc tgttggtgat gaagggcgcc ccagaaagga tcctagaccg ttgcagctct   1560
atcctcctcc acgcaaggga gcagccctg gatgaggagc tgaaagacgc ctttcagaac   1620
gcctatttgg agctgggggg cctcggagaa cgagtcctag gtttctgcca cctcttctg    1680 ccagatgaac agtttcctga agggttccag tttgacactg acgatgtgaa tttccctatc   1740
```

-continued

```
gataatctgt gctttgttgg gctcatctcc atgattgacc ctccacgggc ggccgttcct    1800
gatgccgtgg gcaaatgtcg aagtgctgga attaaggtca tcatggtcac aggagaccat    1860
ccaatcacag ctaaagctat tgccaaaggt gtgggcatca tctcagaagg caatgagacc    1920
gtggaagaca ttgctgcccg cctcaacatc ccagtcagcc aggtgaaccc cagggatgcc    1980
aaggcctgcg tagtacacgg cagtgatcta aaggacatga cctccgagca gctggatgac    2040
attttgaagt accacactga gatagtgttt gccaggacct cccctcagca gaagctcatc    2100
attgtggaag gctgccaaag acagggtgct atcgtggctg tgactggtga cggtgtgaat    2160
gactctccag ctttgaagaa agcagacatt ggggttgcta tggggattgc tggctcagat    2220
gtgtccaagc aagctgctga catgattctt ctggatgaca actttgcctc aattgtgact    2280
ggagtagagg aaggtcgtct gatctttgat aacttgaaga aatccattgc ttataccttg    2340
accagtaaca ttcccgagat caccccgttc ctgatattta ttattgcaaa cattccacta    2400
ccactgggga ctgtcaccat cctctgcatt gacttgggca ctgacatggt tcctgccatc    2460
tccctggctt atgagcaggc tgagagtgac atcatgaaga gacagcccag aaatcccaaa    2520
acagacaaac ttgtgaatga gcggctgatc agcatggcct atgggcagat tggaatgatc    2580
caggccctgg gaggcttctt tacttacttt gtgattctgg ctgagaacgg cttcctccca    2640
attcacctgt tgggcctccg agtggactgg gatgaccgct ggatcaacga tgtggaagac    2700
agctacgggc agcagtggac ctatgagcag aggaaaatcg tggagttcac ctgccacaca    2760
gccttcttcg tcagtatcgt ggtggtgcag tgggccgact tggtcatctg taagaccagg    2820
aggaattcgg tcttccagca ggggatgaag aacaagatct tgatatttgg cctctttgaa    2880
gagacagccc tggctgcttt cctttcctac tgccctggaa tgggtgttgc tcttaggatg    2940
tatcccctca aacctacctg gtggttctgt gccttcccct actctcttct catcttcgta    3000
tatgacgaag tcagaaaact catcatcagg cgacgccctg gcggctgggt ggagaaggaa    3060
acctactatt ag                                                        3072
```